United States Patent
Yilmaz et al.

(10) Patent No.: US 10,694,775 B2
(45) Date of Patent: Jun. 30, 2020

(54) VAPORISABLE MATERIAL AND CAPSULE

(71) Applicant: JT International SA, Geneva (CH)

(72) Inventors: Ugurhan Yilmaz, Konz (DE);
Toshifumi Suzuki, Cologny (CH);
Barry Mooney, Co Antrim (GB);
Tatiana Golovanova, Trier (DE)

(73) Assignee: JT International SA (CH)

( * ) Notice: Subject to any disclaimer, the term of this patent is extended or adjusted under 35 U.S.C. 154(b) by 0 days.

(21) Appl. No.: 16/215,891

(22) Filed: Dec. 11, 2018

(65) Prior Publication Data

US 2019/0104760 A1    Apr. 11, 2019

Related U.S. Application Data (63) Continuation of application No. 14/888,320, filed as application No. PCT/EP2014/058993 on May 2, 2014, now abandoned.

(30) Foreign Application Priority Data

May 2, 2013 (EP) .................................. 13166240.5

(51) Int. Cl.
| | | |
|---|---|---|
| *A24F 47/00* | (2020.01) | |
| *A24B 13/02* | (2006.01) | |
| *A24B 15/167* | (2020.01) | |
| *A24B 15/10* | (2006.01) | |
| *A24B 15/16* | (2020.01) | |

(Continued)

(52) U.S. Cl.
CPC ................. *A24B 13/02* (2013.01); *A24B 7/00* (2013.01); *A24B 9/00* (2013.01); *A24B 15/10* (2013.01); *A24B 15/16* (2013.01); *A24B 15/167* (2016.11); *A24F 40/20* (2020.01); *A24F 47/002* (2013.01); *A24F 47/004* (2013.01); *A61M 15/06* (2013.01);
(Continued)

(58) Field of Classification Search
CPC ....................................................... A24B 3/14
See application file for complete search history.

(56) References Cited

U.S. PATENT DOCUMENTS

| | | |
|---|---|---|
| 2004/0118421 A1 | 6/2004 | Hodin et al. |
| 2009/0151717 A1 | 6/2009 | Bowen et al. |

(Continued)

FOREIGN PATENT DOCUMENTS

| | | |
|---|---|---|
| GB | 983928 A | 2/1965 |
| GB | 1315086 A | 4/1973 |

(Continued)

OTHER PUBLICATIONS

International Search Report for Application No. PCT/EP2014/058993 dated Jul. 7, 2014.

(Continued)

*Primary Examiner* — Eric Yaary
(74) *Attorney, Agent, or Firm* — Lerner, David, Littenberg, Krumholz & Mentlik, LLP (57) ABSTRACT

A method for producing a vaporisable material comprising plant fibres for use in a vapour generating device which generates a vapour by heating the vaporisable material is disclosed. The method comprises reducing the particle size of the plant fibres to less than 1.5 mm and mixing plant fibres of at least two ranges of particle size. The invention also relates to vaporisable material for use in a vapour generating device obtainable by the method.

13 Claims, 6 Drawing Sheets

(51) Int. Cl.
*A61M 15/06* (2006.01)
*A24F 40/20* (2020.01)
*A24B 7/00* (2006.01)
*A24B 9/00* (2006.01)
*A61M 11/04* (2006.01)

(52) U.S. Cl.
CPC .......... *A61M 11/042* (2014.02); *A61M 11/048* (2014.02)

(56) References Cited

U.S. PATENT DOCUMENTS

| | | | |
|---|---|---|---|
| 2009/0293889 A1 | 12/2009 | Kumar et al. | |
| 2009/0293892 A1* | 12/2009 | Williams | A24F 47/008 131/328 |
| 2010/0024834 A1 | 2/2010 | Oglesby et al. | |
| 2011/0220130 A1 | 9/2011 | Mua et al. | |
| 2013/0186416 A1 | 7/2013 | Gao et al. | |
| 2014/0076337 A1* | 3/2014 | Woodman | A24F 47/006 131/280 |
| 2014/0166032 A1* | 6/2014 | Gindrat | A24B 15/12 131/353 |

FOREIGN PATENT DOCUMENTS

| | | |
|---|---|---|
| JP | 2000224978 A | 8/2000 |
| JP | 2007507231 A | 3/2007 |
| JP | 2011505874 A | 3/2011 |
| JP | 5184675 B2 | 4/2013 |
| JP | 2013513399 A | 4/2013 |
| WO | 2005032285 A1 | 4/2005 |
| WO | 2009079641 A2 | 6/2009 |

OTHER PUBLICATIONS

AZoM, Particle Size—US Sieve Series and Tyler Mesh Size Equivalents, https://www.azom.com/article.aspx?ArticleD=1417, May 15, 2002.

Japanese Office Action for Japanese Application No. 2016511094 dated Oct. 30, 2018.

* cited by examiner

VAPORISABLE MATERIAL AND CAPSULE

CROSS-REFERENCE TO RELATED APPLICATIONS

This application is a continuation of U.S. application Ser. No. 14/888,320, filed on Oct. 30, 2015, which is a national phase entry under 35 U.S.C. § 371 of International Application No. PCT/EP2014/058993, filed May 2, 2014, which claims priority from EP Patent Application No. 13166240.5 filed May 2, 2013, all of which are incorporated herein by reference.

BACKGROUND OF THE INVENTION

The present invention relates to a vaporisable material and a vaporisable material-containing capsule for use in a vapour generating device. Devices which heat rather than burn vaporisable material such as tobacco, to create a vapour for inhalation are becoming popular. They generally comprise a heat source powered by gas or electricity and a chamber for receiving a plug of vaporisable material or a disposable capsule containing a vapour-generating product. In use the plug or capsule is inserted into the device and heated by the heat source to generate a vapour for inhalation. An example of such a device can be found in described in PCT publication WO 2009/079641.

Such devices have become popular because they can provide a user with an experience very similar to smoking the vaporisable material but without the burning of plant material such as tobacco.

However, such devices are not always popular with consumers because they can produce inconsistent levels of vapour and are often unreliable in terms of the length of use of an individual capsule, leaving to an inconsistency of flavour delivery to a user. Since the material is heated, rather than being burned, it is important to provide a method of preparation of this vaporisable material that preserves its aroma.

In addition, there is a need to provide a vaporisable material that can be designed to provide either a high or a low level of taste and/or a short or long lasting taste to a user.

The present invention seeks to provide a vaporisable material and capsule containing such a material, which overcomes at least some of these problems.

BRIEF SUMMARY OF THE INVENTION

According to a first aspect, the present invention provides a method for producing a vaporisable material comprising plant fibres for use in a vapour generating device which generates a vapour by heating the vaporisable material, the method comprising the step of reducing the particle size of the plant fibres to less than 1.5 mm and comprising a further step of mixing plant fibres of at least two ranges of particle size.

According to a second aspect, the present invention provides a method for producing a vaporisable material comprising plant fibres for use in a vapour generating device which generates a vapour by heating the vaporisable material, the method comprising the step of reducing the particle size of the plant fibres by cutting the fibres and further characterised in that the plant fibres are not crushed.

According to a third aspect, the present invention provides vaporisable material for use in a vapour generating device, the material being obtainable by the method according to the first or second aspects of the invention.

According to a fourth aspect, the present invention provides a capsule containing vaporisable material according to the third aspect of the invention.

DETAILED DESCRIPTION

A first aspect of the invention is directed to a vaporisable material suitable for use in a vapour generating device wherein the material comprises a blend of different particle sizes, which enables high impact/fast delivery particles to be mixed with low impact/longer delivery time particles. This blend of different particle sizes results in an improvement in the richness and smoothness of the flavour when inhaled using the vapour-generating device, as perceived by the end user, as well as in improvement in the duration of delivery of the desired taste level.

The term "taste" has its usual meaning in the context of the present invention, and refers to the chemical sensation produced when inhaled vapours produced by heating the vaporisable material reacts chemically with taste bud receptors in the mouth of a user. The sensation of taste can be categorized into five basic tastes: sweetness; sourness; saltiness; bitterness; and umami. Taste, along with smell (olfaction) and trigeminal nerve stimulation, determines perception of flavours. The term "flavour" also has its usual meaning and refers to the sensory impression of inhaled vapours perceived by the user. Flavour is determined mainly by the chemical senses of taste and smell.

A vaporisable material having the required particle size blend is obtainable by the method according to the first aspect of the invention, which comprises the step of reducing the particle size of the plant fibres to less than 1.5 mm. Preferably, the particle size of the plant fibres is reduced to less than 0.85 mm.

As used herein, the term "vaporisable" has its usual meaning in the art, referring to a material that is capable of being converted from a solid or liquid state to a gaseous state upon heating.

As used herein, the term "particle size" refers to the largest dimension of a particle, which determines the smallest mesh pore diameter that the particle will be able to pass through when sieved.

The vaporisable material comprises plant fibres, and preferably comprises tobacco. Examples of suitable forms of tobacco include leaf, STEM, expanded tobacco blend and reconstituted tobacco blend. The vaporisable material may also contain additives such as flavouring agents.

The vaporisable material of the invention is suitable for use in a vapour-generating device, such as a tobacco-heating device. An example of such a device can be found in PCT publication WO 23091079641.

The particle size of the plant fibres is reduced to within the required range by grinding, crushing or cutting the fibres. Preferably, the fibres are cut, and preferably are cut using a cutting mill.

Preferably, the method comprises a further step of sieving the cut plant fibres to separate into fibres of different particle sizes. Examples of suitable mesh pore diameters include: 0.85, 0.60, 0.40 and 0.25 mm, however these can be varied. Once the cut fibres having been separated according to their particle size by sieving, the method of the invention preferably comprises mixing cut plant fibres of at least two ranges of particle size, preferably more than two. For example, fibres having a particle size in the range of 0.85-0.60 mm may be mixed with fibres having a particle size of 0.40-0.25 mm.

The product obtained by the method of the invention may comprise a range of cut plant fibres having particle sizes ranging from 0.85 to 0.25 mm. Examples of particle size distributions are shown in Table 1.

TABLE 1

| Sieve pore size (mm) | I | II | III |
|---|---|---|---|
| 0.85-0.60 | 10% | 10% | 10% |
| 0.60-0.40 | 20% | 20% | 50% |
| 0.40-0.25 | 20% | 50% | 30% |
| 0.25-pan | 50% | 20% | 10% |

Examples of blends of different particle sizes which result in improved richness and smoothness of the taste of a vaporisable tobacco material, as judged by a panel of regular tobacco users, are shown in Table 2.

TABLE 2

| Sieve pore size (mm) | I | II | III |
|---|---|---|---|
| 0.85-0.60 | 10% | 10% | 10% |
| 0.60-0.40 | 20% | 20% | 50% |
| 0.40-0.25 | 20% | 50% | 30% |
| 0.25-pan | 50% | 20% | 10% |
| Comment on effect: | | | |
| Tobacco taste | weak | weak-medium | medium |
| Duration | long | long | Long-medium |

Examples of blends of different particle sizes which result in improvement in the duration of delivery of the desired taste level are shown in Table 3.

TABLE 3

| Sieve pore size (mm) | Rich tobacco taste | Smooth tobacco taste |
|---|---|---|
| 0.85-0.60 | 20% | 10% |
| 0.60-0.40 | 30% | 30% |
| 0 40-0.25 | 30% | 30% |
| 0.25-pan | 20% | 30% |

Optionally, at least one humectant is added to the out plant fibres. A humectant is a hygroscopic substance that has an affinity to form hydrogen bonds with molecules of water and is used to produce a visible exhaled aerosol (i.e. vapour) when the product is in use. Suitable humectants for inclusion in a final vaporizable product according to the present invention include propylene glycol. also known as 1,2-propanediol or propane-1,2-diol and having the formula $C_3H_8O_2$ or $HO-CH_2-CHOH-CH_3$, and glycerol, also known as glycerine and having the formula $C_3H_8O_3$. In a preferred embodiment, the humectant is propylene glycol. Preferably, the final vaporisable product comprises at least 20 wt % humectant, and preferably the amount of humectant present is from 20 to 60 wt %, most preferably about 50 wt %.

The method of the invention may also comprise a step of drying the plant fibres to obtain a pre-determined moisture content. It is preferred that the drying step is implemented before the step of reducing the particle size of the plant fibres, as this facilitates particle size reduction (e.g. by cutting). However, the drying step could also be implemented after the particle size reduction step or after the sieving step. The drying step is preferably carried out using an oven which dries the substances mainly by conduction as a batch process. Alternatively other types of dryers such as rotary dryer, flash dryer, radio frequency dryer can also be used as a continuous process.

As used herein, the term "moisture content" refers to the amount of moisture (i.e. water) present in a given material, e.g. vaporisable material including plant material and fibres such as tobacco. The dried Want fibres preferably have a moisture content of about 5 wt % or less. preferably from about 1 to 5 wt %, more preferably from about 3 to 5 wt % and most preferably about 4 wt %.

The skilled person will be familiar with suitable methodologies for determining the moisture content of a given material and will appreciate that different methodologies are applicable to different materials. For the avoidance of doubt, a method for determining the moisture content of a material comprising dried plant fibres such as tobacco is described as follows:

A heat source, preferably a halogen lamp, is set to a temperature of 105° C. and ~2 g of dried tobacco sample is placed in a weighing chamber and heated by the lamp. The weight of the sample due moisture loss is measured until a constant weight is reached. The moisture content is calculated by subtracting the dried sample weight ($W_D$) from the initial sample weight ($W_I$), dividing by the dried sample weight, and multiplying by 100:

$$\frac{W_D - W_I}{W_D} \times 100$$

In a preferred embodiment, the method according to the first aspect of the invention comprises the following steps:
   i. drying the plant fibres to a pre-determined moisture content;
   ii. cutting the plant fibres;
   iii. sieving the cut plant fibres after the cutting step to separate fibres of different particle sizes;
   iv. adding at least one humectant to the plant fibres; and
   v. mixing the dried sieved cut plant fibres with the humectants.

The present invention also relates to a vaporisable material obtainable by the above-described method. The material obtained is suitable for use in a vapour-generating device, such as a tobacco heating device.

Another aspect of the present invention provides a method for producing a vaporisable material comprising plant fibres for use in a vapour-generating device which generates a vapour by heating the vaporisable material, comprising the step of reducing the particle size of the plant fibres by cutting the fibres. This method is further characterised in that the plant fibres are not crushed or ground.

Preferably the plant fibres are cut using a cutting mill, such as a Hosokawa Alpine Rotoplex-Schneidmühle Ro 28/40, using scissors to reduce the particle size.

The advantage of cutting, rather than crushing or grinding, the plant fibres is that the aroma is retained within the material and is not released before use. This results in an improved taste and flavour delivery to an end user. Preferably, the plant fibres are cut to produce particle sizes of less than 1.5 mm, preferably to produce particle sizes ranging from 0.85 to 0.25 mm.

This method according to this aspect of the invention may optionally include one or more of the method steps described above in relation to the first aspect of the invention.

The present invention also relates to a vaporisable material obtainable by this method. The material obtained is suitable for use in a vapour-generating device, such as a tobacco heating device.

The vaporisable material obtained by either method of the present invention is preferably in a sealed package, which provides an absolute bather enabling the moisture content and flavour of the product to be retained over time. The term "sealed package" refers to a gas-impermeable container having a hermetic closure and in the context of the present invention is preferably a capsule. Ideally, the product comprising vaporisable material should be processed and packaged as quickly as possible to ensure that atmospheric moisture is not absorbed into the material.

Figure 1:
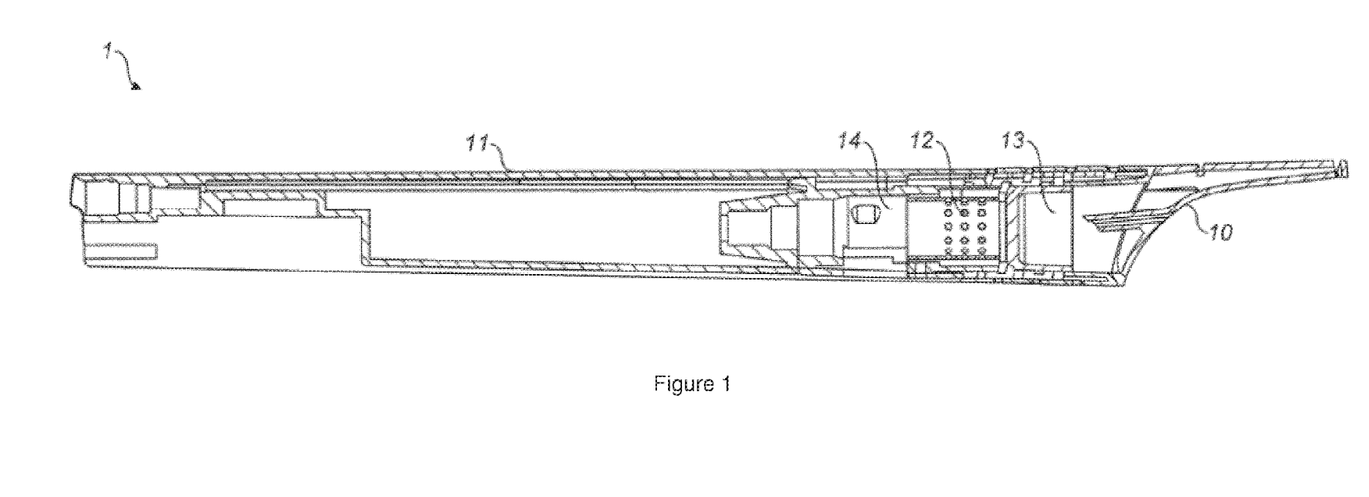
FIG. 1 is a side cross-sectional schematic view of a heating device comprising a capsule according to the present invention.

Referring to FIG. 1, there is shown a tobacco heating device 1 of the type generally described in PCT publication WO 2009/079641. The device has a mouthpiece 10, body 11, heater 12, heating chamber 13 and a fuel supply 14. The device also usually has control components to regulate the temperature of the device particularly within the heating chamber to control a container 20 placed within the device in use. Whilst this example device uses a combustible fuel as a heat source, it will be appreciated that the device may have another type of heat source and power supply, such as an electrical heater and battery, for example.

In use a capsule 20 is inserted into the heating chamber 13, and the heater 12 supplied with fuel from the fuel tank 14 to heat the heating chamber 13, under the control of a user. The capsule 20 contains a plug of vaporisable material obtained by a method according to the present invention. The contents of the capsule are heated by the heater 12 to create an aerosol vapour based on the contents of the container, that aerosol then being inhaled by the user via the mouth piece 10.

Figure 2:
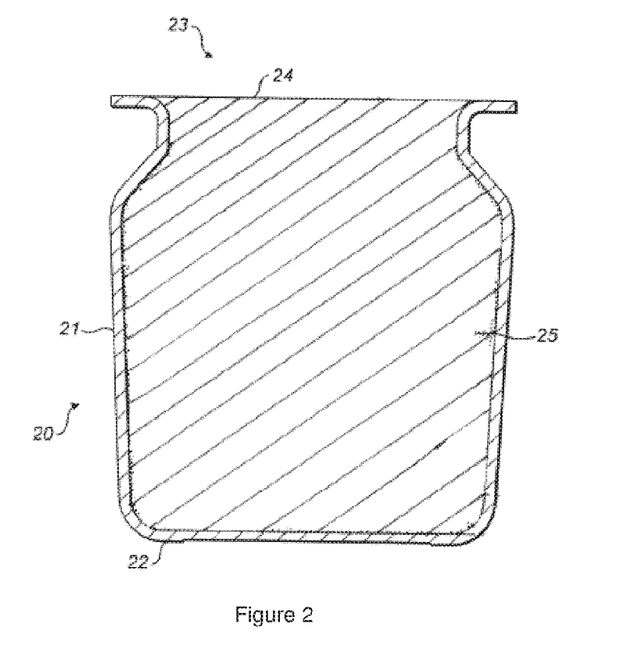
FIG. 2 is a side cross-sectional view through a plug and capsule in accordance with the invention.

Referring to FIG. 2, a plug of vaporisable material 25 obtained by a method according to the present invention is shown. In this example the plug is provided in a capsule 20. It is possible to provide the plug in a user-removable wrapper which is taken off prior to insertion of the plug 25 into the heating chamber 13 of the device 1 or to supply the plug 25 in a dispenser which inserts the plug 25 into the device 1 to avoid handling by a user.

The invention is further described by reference to the following non-limiting example.

Example

The effect of preparing vaporisable material comprising tobacco fibres of different particle sizes was investigated by the inventors. The consistency of release of compounds (propylene glycol (PG) and total particulate matter (TPM)) during smoking was compared for a range of products comprising plant fibres of different particle sizes.

Test samples were prepared as shown in Table 4:

TABLE 4

| Particle size (mm) | Sample | | | | | | | | |
|---|---|---|---|---|---|---|---|---|---|
| | A | B | C | D | E | F | G | H | I |
| 0.85-0.60 | 0% | 50% | 50% | 50% | 10% | 10% | 10% | 20% | 10% |
| 0.60-0.40 | 0% | 50% | 0% | 0% | 20% | 20% | 50% | 30% | 30% |
| 0.40-0.25 | 50% | 0% | 50% | 0% | 20% | 50% | 30% | 30% | 30% |
| <0.25 | 50% | 0% | 0% | 50% | 50% | 20% | 10% | 20% | 30% |

A negative control sample (sample J) was prepared as shown in Table 5:

TABLE 5

| Particle size (mm) | Sample J (control) |
|---|---|
| 2.5-1.6 | 100% |
| 0.85-0.60 | 0% |
| 0.60-0.40 | 0% |
| 0.40-0.25 | 0% |
| <0.25 | 0% |

PG yield was analysed by gas chromatography using a flame ionization detector (GC-FID). The methodology used is similar to 15010315, which is the standard protocol for gas-chromatographic determination of nicotine in cigarette smoke condensates. Details of ISO10315 are available at http://www.iso.org/iso/home.html. This test protocol is representative of the PG yield H exhaled vapour of a smoking device containing vaporisable material in use. Specifically, PG yield was measured in vapour exhaled in puffs 5, 10, 15 and 20 as shown in Table 6:

TABLE 6

| CFP* (44 mmφ) | CFP* (44 mmφ) | | | |
|---|---|---|---|---|
| (level) | Puff volume | Puff duration | Puff interval | Puff number |
| 1 | 55 mL | 2 seconds | 30 seconds | 5 |
| 2 | 55 mL | 2 seconds | 30 seconds | 10 |
| 3 | 55 mL | 2 seconds | 30 seconds | 15 |
| 4 | 55 mL | 2 seconds | 30 seconds | 20 |

*Cambridge Filter Pad

Quantitative analysis was carried out using n-Octadecane extraction, according to the parameters shown in Table 7:

TABLE 7

| | |
|---|---|
| Target | PG |
| Analytical instrument | GC-FID |
| Column | DB-WAX (15 mx 350 um) |
| oven temperature | 80° C. (1 min) - 10° C./min - 150° C.-(20° C./min) |
| | 190° C. (3 min) - 70° C./min- 250° C. (5 min) |
| Carrier gas | He 20 mL/min |
| Injection volume | 1μ 1μ (split ratio 2:1) |
| Injection temperature | 250° C. |
| Detector | FID 250° C. 20 Hz |
| | H₂ 40 mL/min |
| | Air 450 mL/min |
| Range of standard solutions | 0.2-6 mg/mL |
| | Conversion; 2-60 mg/pod |

Figure 3:
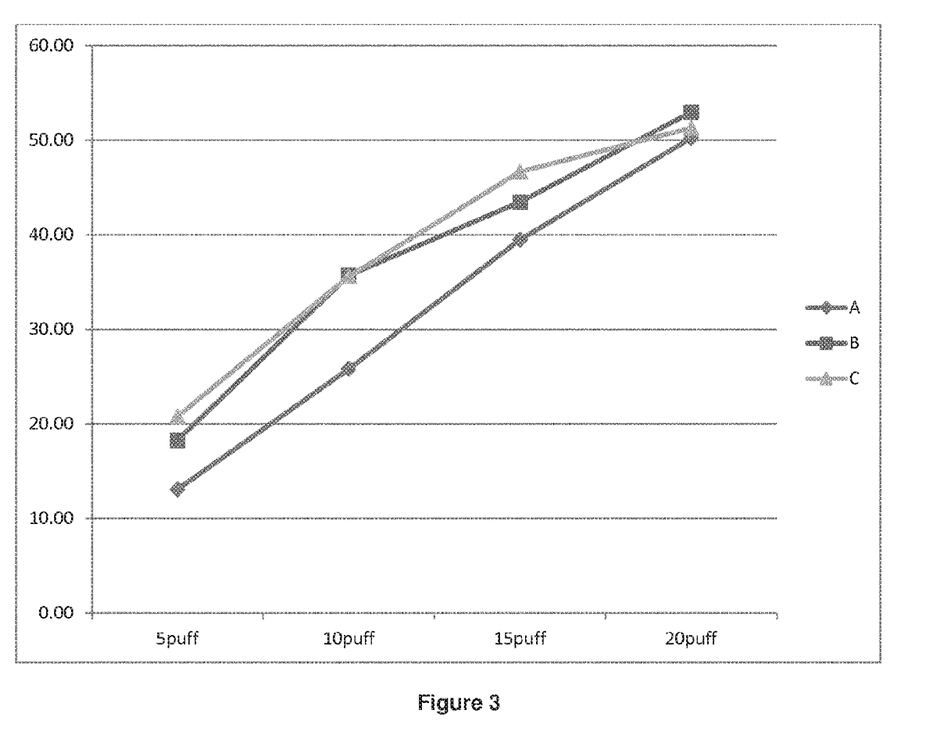
FIG. 3 is a graph showing the total propylene glycol (PG) yield at puffs 5, 10, 15 and 20 for test samples A, B and C.
Figure 4:
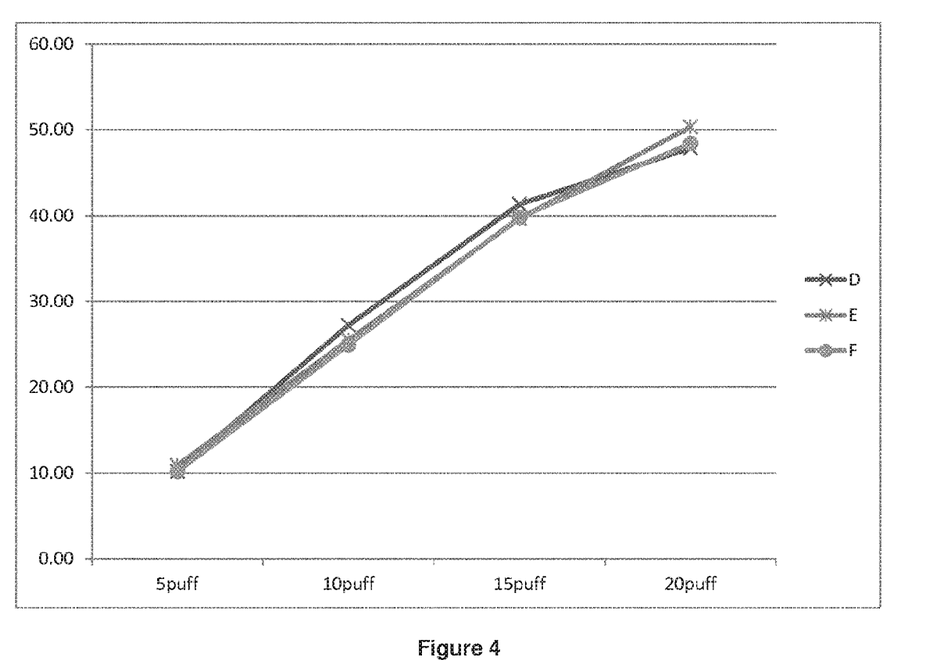
FIG. 4 is a graph showing the PG yield at puffs 5, 10, 15 and 20 for test samples D, E and F.
Figure 5:
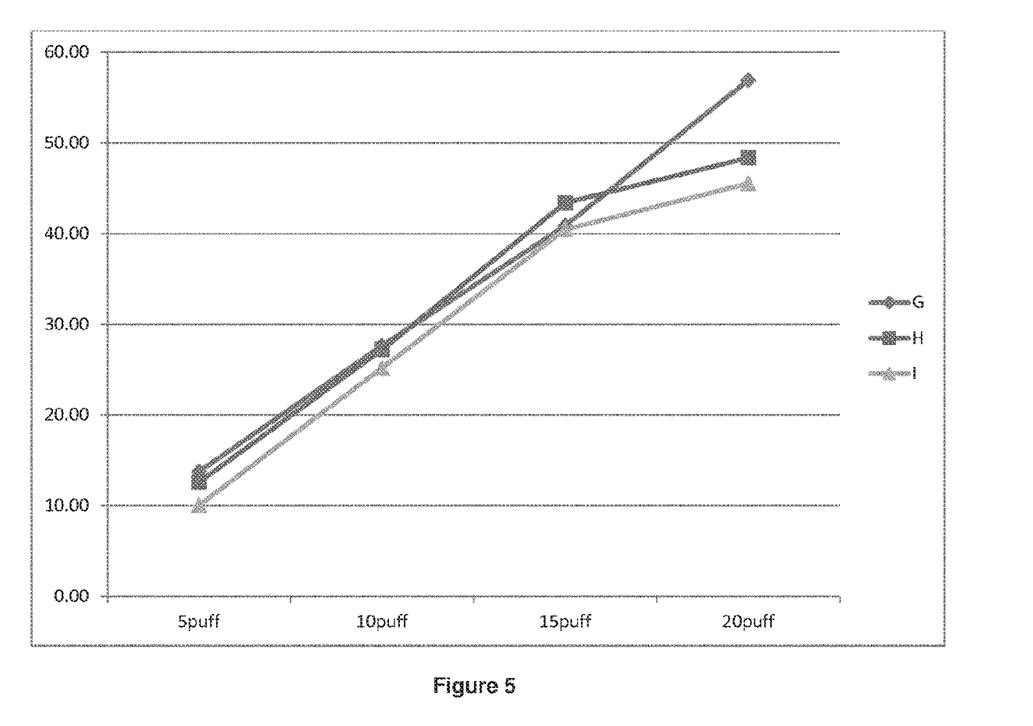
FIG. 5 is a graph showing the PG yield at puffs 5, 10, 15 and 20 for test samples G, H and I.
Figure 6:
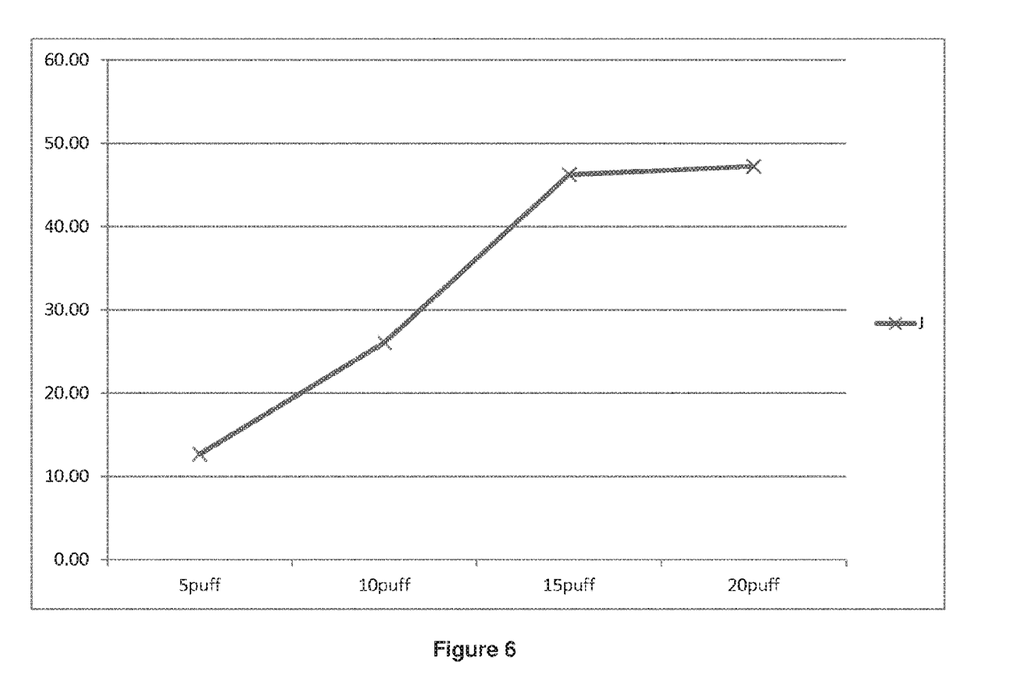
FIG. 6 is a graph showing the total PG yield at puffs 5, 10, 15 and 20 for the negative control sample J.

The data in FIGS. 3-5 show the PG yield (mg/pod) in exhaled vapour for samples A, B, C, D. E and F measured in puffs 5, 10, 15 and 20. These graphs show the PG yield increasing steadily as the tobacco product is smoked. In contrast, FIG. 6 shows the same data for the negative control product (sample J). It is clear from this graph that the PG yield in exhaled smoke ceases to increase steadily beyond puff 15, as shown by the flat line between puffs 15 and 20.

This data supports the subjective experience of a panel of regular tobacco users, and is evidence that vaporisable material prepared according to the method of the invention provides consistent release of compounds when in use which correlates to improved duration of delivery of the desired taste and flavour. PG is an objective marker of choice to support the subjective experience data because PG is one of the main compounds that is used as a carrier of other compounds in the vapour.

As shown by FIG. 6, when the particle sizes of the plant fibres are outside of the range of the invention, released compound yield (and consequently the delivery of the desired taste and flavour) begins to decline after about 15 puffs. Assuming approximately 40 puffs are taken when smoking the tobacco product (based on a smoking rate of 2 puffs/minute for 20 minutes), this means that the quality of the negative control product, as perceived by a user, beings to decline less than half way through use.

FIGS. 3-5 show that when the particle sizes of the plant fibres are within the range of the present invention, released compound yield (and consequently the delivery of the desired taste and flavour) is maintained for longer, providing an improved user experience.

Figure 7:
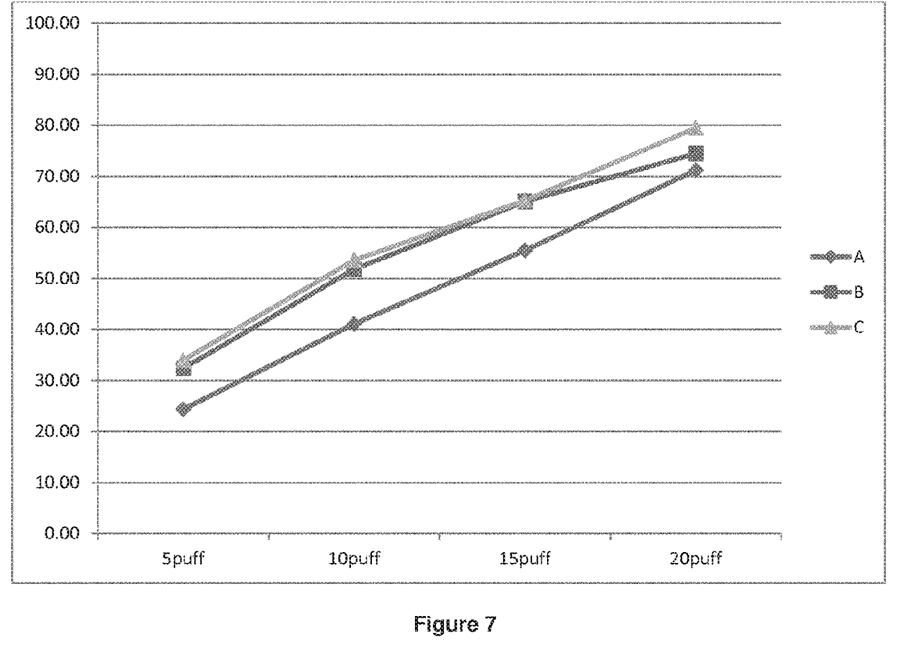
FIG. 7 is a graph showing the total particulate matter (TPM) yield at puffs 5, 10, 15 and 20 for test samples A, B and C.
Figure 8:
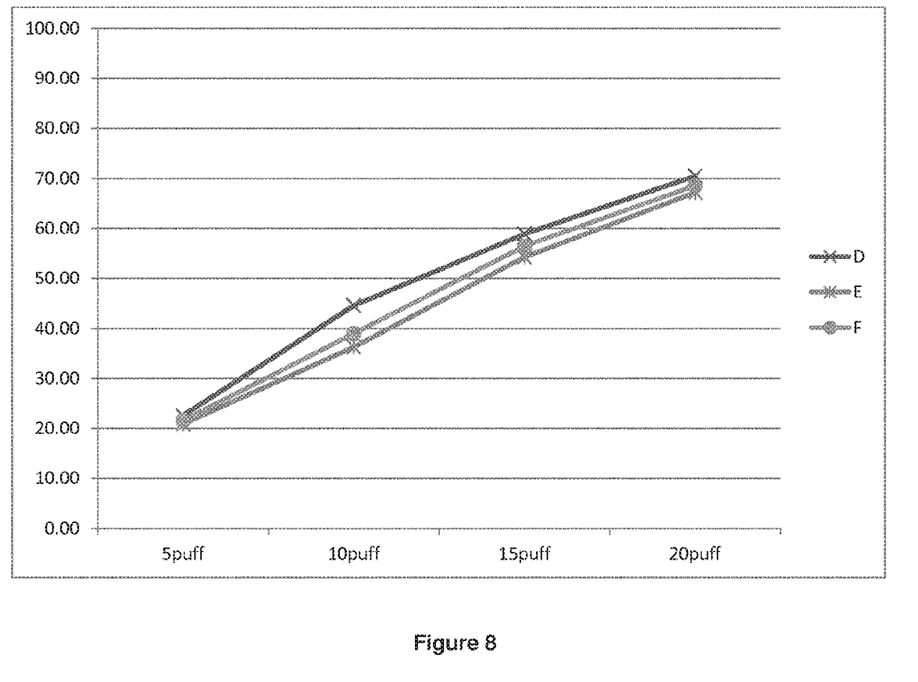
FIG. 8 is a graph showing the TPM yield at puffs 5, 10, 15 and 20 for test samples D, E and F.
Figure 9:
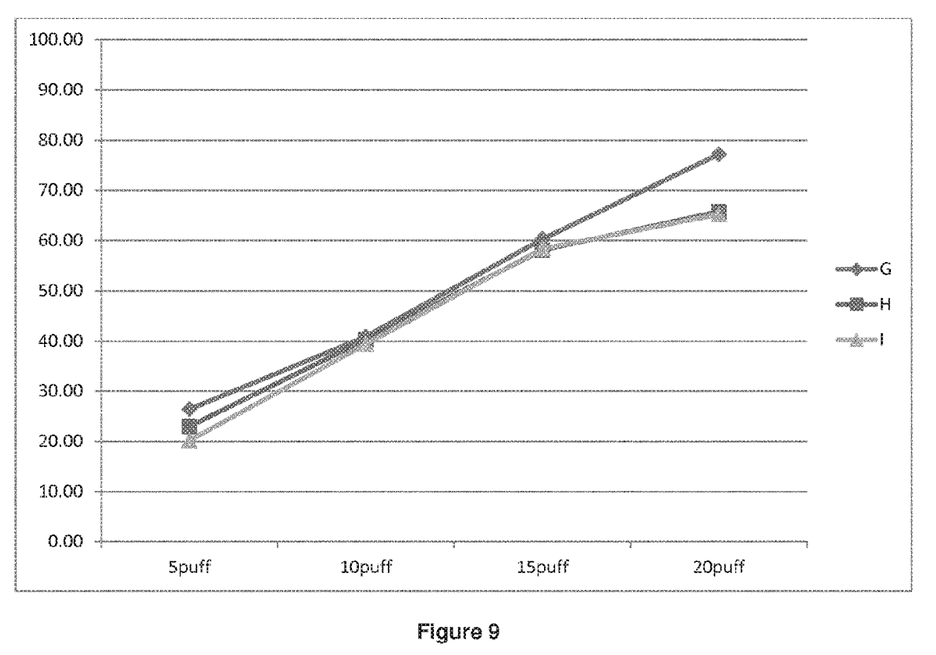
FIG. 9 is a graph showing the TPM yield at puffs 5, 10, 15 and 20 for test samples G, H and I.
Figure 10:
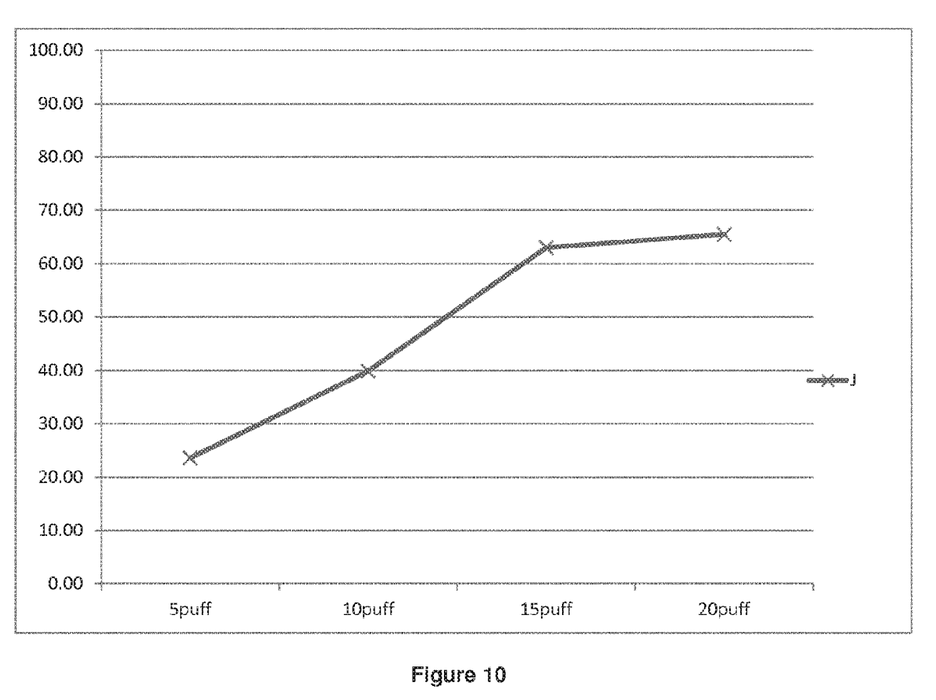
FIG. 10 is a graph showing the TPM yield at puffs 5, 10, 15 and 20 for the negative control sample J.

FIGS. 7-9 show data for total particulate matter (TPM) corresponding to FIGS. 3-5. Again, these graphs show that when the particle sizes of the plant fibres are within the range of the present invention the TPM yield (mg/pod) increases steadily as the tobacco product is smoked. In contrast, FIG. 10 shows the same TPM data for the negative control product (sample J). It is clear from this graph that the TPM yield in exhaled smoke ceases to increase steadily beyond puff 15, as shown by the flat line between puffs 15 and 20.

This TPM data also supports the subjective experience of a panel of regular tobacco users, and is evidence that vaporisable material prepared according to the method of the invention provides consistent release of compounds correlating to improved duration of delivery of the desired taste and favour of the tobacco product.

The invention claimed is:

1. A vapour generating device, comprising a plug of a vaporisable material, wherein the vaporisable material comprises tobacco, and a humectant in the presence of at least 20 wt %,
wherein the tobacco has particle sizes in each range of 0.85 mm to 0.60 mm, 0.60 mm to 0.40 mm, 0.40 mm to 0.25 mm, and less than 0.25 mm, and the particle sizes in the range of 0.60 mm to 0.40 mm is in an amount of at least 50 wt %.

2. The vapour generating device of claim 1, wherein the humectant is in the presence of 20 wt % to 60 wt %.

3. The vapour generating device of claim 1, wherein the humectant is in the presence of about 50 wt %.

4. The vapour generating device of claim 1, wherein the tobacco has a moisture content of about 5 wt % or less.

5. The vapour generating device of claim 1, wherein the tobacco has a moisture content of about 1 wt % to about 5 wt %.

6. The vapour generating device of claim 1, wherein the tobacco has a moisture content of about 3 wt % to about 5 wt %.

7. The vapour generating device of claim 1, wherein the tobacco has a moisture content of about 4 wt %.

8. The vapour generating device of claim 7, wherein the tobacco is in the form of leaf, STEM, expanded tobacco blend, reconstituted tobacco blend, or a combination thereof.

9. The vapour generating device of claim 1, wherein the humectant is 1, 2-propanediol or glycerol.

10. A method of producing a vapour in a vapour generating device, the method comprising:
supplying a plug of a vaporisable material into a heating chamber of a vapour generating device, wherein the vaporisable material comprises tobacco, and a humectant in the presence of at least 20 wt %, and
heating the heating chamber by a heat source,
wherein the tobacco has particle sizes in each range of 0.85 mm to 0.60 mm, 0.60 mm to 0.40 mm, 0.40 mm to 0.25 mm, and less than 0.25 mm, and the particle sizes in the range of 0.60 mm to 0.40 mm is in an amount of at least 50 wt %.

11. The method of claim 10, wherein the humectant is in the presence of 20 wt % to 60 wt %.

12. The method of claim 10, wherein the tobacco has a moisture content of about 5 wt % or less.

13. The method of claim 10, wherein the tobacco has a moisture content of about 1 wt % to about 5 wt %.

* * * * *